(12) United States Patent
Rothman et al.

(10) Patent No.: US 8,057,522 B2
(45) Date of Patent: Nov. 15, 2011

(54) METHODS AND APPARATUS FOR PROVIDING A RETAINER FOR A BONE STABILIZATION DEVICE

(75) Inventors: Richard H. Rothman, Philadelphia, PA (US); Rafail Zubok, Midland Park, NJ (US); Mikhail Kvitnitsky, Clifton, NJ (US)

(73) Assignee: Altus Partners, LLC, Newton Square, PA (US)

( * ) Notice: Subject to any disclaimer, the term of this patent is extended or adjusted under 35 U.S.C. 154(b) by 379 days.

(21) Appl. No.: 12/397,935

(22) Filed: Mar. 4, 2009

(65) Prior Publication Data
US 2009/0171397 A1 Jul. 2, 2009

Related U.S. Application Data

(62) Division of application No. 11/348,594, filed on Feb. 7, 2006, now abandoned.
(60) Provisional application No. 60/658,313, filed on Mar. 3, 2005.

(51) Int. Cl.
*A61B 17/80* (2006.01)
(52) U.S. Cl. .......................................... 606/289; 606/71
(58) Field of Classification Search .............. 606/60, 606/280, 70, 286–296, 246
See application file for complete search history.

(56) References Cited

U.S. PATENT DOCUMENTS

| 5,261,910 A | 11/1993 | Warden et al. |
| 6,224,602 B1 | 5/2001 | Hayes |
| 6,258,089 B1 | 7/2001 | Campbell et al. |
| 6,261,291 B1 | 7/2001 | Talaber et al. |
| 6,306,139 B1 | 10/2001 | Fuentes |
| 6,361,537 B1 | 3/2002 | Anderson |
| 6,599,290 B2 | 7/2003 | Bailey et al. |
| 6,602,255 B1 | 8/2003 | Campbell et al. |
| 6,626,907 B2 | 9/2003 | Campbell et al. |

(Continued)

FOREIGN PATENT DOCUMENTS

WO 2005011508 5/2005

OTHER PUBLICATIONS

Neurosurg Focus 12 (1): Article 15, 2002, "The Cervical Spine Study Group anterior cervical plate nomenclature" by Regis W. Hain, MD., et al., Department of Neurosurgery.

(Continued)

*Primary Examiner* — Eduardo C Robert
*Assistant Examiner* — Ellen C Hammond
(74) *Attorney, Agent, or Firm* — Matthew B. Dernier, Esq.; Gibson & Dernier LLP (57) ABSTRACT

A skeletal fixation apparatus includes: a plate having first and second spaced apart surfaces and a plurality of apertures extending through the surfaces of the plate, each aperture for receiving a respective fixation element for coupling the plate to one or more bones of a patient; and at least one retention element having an elongate member coupled to the plate at first and second ends thereof, wherein the first end of the elongate member is fixed in position and the second end of the elongate member is operable to rotate about the first end such that: (i) at least a portion of the elongate member overlies at least a portion of a first of the apertures when the second end is in at least one first rotational position to retain a first fixation element in the first aperture, and (ii) the elongate member does not substantially overlie the first aperture when the second end is in at least one second rotational position to permit the first fixation element to enter or exit the first aperture.

14 Claims, 6 Drawing Sheets

U.S. PATENT DOCUMENTS

| | | | |
|---|---|---|---|
| 6,755,833 B1 | 6/2004 | Paul et al. |
| 7,025,769 B1 | 4/2006 | Ferree |
| 7,306,605 B2 | 12/2007 | Ross |
| 7,318,825 B2 | 1/2008 | Butler et al. |
| 7,481,811 B2 | 1/2009 | Suh |
| 2004/0087951 A1 | 5/2004 | Khalili |
| 2004/0097934 A1 | 5/2004 | Farris et al. |
| 2004/0153069 A1 | 8/2004 | Paul |
| 2005/0010227 A1 | 1/2005 | Paul |
| 2005/0021032 A1 | 1/2005 | Koo |
| 2005/0192577 A1 | 9/2005 | Mosca et al. |

OTHER PUBLICATIONS

International Preliminary Report on Patentability and Written Opinion for corresponding PCT application PCT/US2006/004154.

METHODS AND APPARATUS FOR PROVIDING A RETAINER FOR A BONE STABILIZATION DEVICE

CROSS REFERENCE TO RELATED APPLICATIONS

This application is a divisional application of U.S. patent application Ser. No. 11/348,594, filed on Feb. 7, 2006, now abandoned, which claims the benefit of U.S. Provisional Patent Application No. 60/658,313, filed Mar. 3, 2005, each of which is hereby incorporated by reference in its entirety.

BACKGROUND OF THE INVENTION

The present invention is directed to a screw retainer for a bone plate.

Back pain is one of the most common and often debilitating conditions affecting millions of people in all walks of life. Today, it is estimated that over ten million people in the United States alone suffer from persistent back pain. Approximately half of those suffering from persistent back pain are afflicted with chronic disabling pain, which seriously compromises a person's quality of life and is the second most common cause of worker absenteeism. Further, the cost of treating chronic back pain is very high, even though the majority of sufferers do not receive treatment due to health risks, limited treatment options and inadequate therapeutic results. Thus, chronic back pain has a significantly adverse effect on a person's quality of life, on industrial productivity, and on heath care expenditures.

Degenerative spinal column diseases, such as disc degenerative diseases (DDD), spinal stenosis, spondylolisthesis, and so on, need surgical operation if they do not take a turn for the better by conservative management. Typically, spinal decompression is the first surgical procedure that is performed. The primary purpose of decompression is to reduce pressure in the spinal canal and on nerve roots located therein by removing a certain tissue of the spinal column to reduce or eliminate the pressure and pain caused by the pressure. If the tissue of the spinal column is removed the pain is reduced but the spinal column is weakened. Therefore, fusion surgery (e.g., ALIF, PLIF or posterolateral fusion) is often necessary for spinal stability following the decompression procedure. However, following the surgical procedure, fusion takes additional time to achieve maximum stability and a spinal fixation device is typically used to support the spinal column until a desired level of fusion is achieved. Depending on a patient's particular circumstances and condition, a spinal fixation surgery can sometimes be performed immediately following decompression, without performing the fusion procedure. The fixation surgery is performed in most cases because it provides immediate postoperative stability and, if fusion surgery has also been performed, it provides support of the spine until sufficient fusion and stability has been achieved.

Conventional methods of spinal fixation utilize a rigid spinal fixation device to support an injured spinal part and prevent movement of the injured part. Among these conventional spinal fixation devices are plates configured to be positioned adjacent to the injured spinal part, and secured to the bone by screws. An increasingly accepted procedure for treating spinal disorders involves using the rigid plates to hold vertebrae in desired spatial relationships and orientations relative to each other. The upper cervical spine can be approached anteriorly or posteriorly. In either case, holes are drilled and tapped in at least two of the vertebrae, to receive screws or other fasteners used to secure the plate. The holes are accurately positioned with reference to openings formed through the cervical plate. In some cases the screws may be self-tapping. Typically the plate is curved about its longitudinal axis to facilitate contiguous surface engagement of the plates with the vertebrae. With the plate maintained against the vertebrae, the fasteners are secure within the holes. As a result, the plate maintains the attached vertebrae in a desired spacing and orientation with respect to each other.

One of the problems associated with this technique is the tendency of screws or other fasteners to gradually work loose after fixation. Slight shock or vibration of the vertebrae, due to walking, climbing stairs or more vigorous activity by the patient following treatment increases this tendency, jeopardizing the integrity of fixation. Moreover, as the fasteners work loose, the outward protrusion of the heads over other components of the fasteners can be a source of discomfort and present the risk of trauma to adjacent and surrounding soft tissue.

The curvature of cervical plates typically results in a convergence of fasteners that extend through spaced apart openings in the plate, particularly when each screw is perpendicular to the region of the plate surrounding it. Screws sufficiently short to avoid interfering with one another may not be long enough to assure a secure plate fixation. Further, the physician may encounter difficulties in positioning the plate if one of the vertebrae, due to a particular shape and orientation, cannot readily retain a perpendicularly inserted fastener.

There have been attempts to solve the above problems. For example, screws or other fasteners can be provided with somewhat rounded heads as shown in U.S. Pat. No. 5,324,290. U.S. Pat. No. 5,261,910 shows a nut with a rounded upper surface and a hexagonal recess. The nut has a conical portion that fits into a similarly shaped recess in a plate, thus to reduce the height at which the nut extends above the plate. U.S. Pat. No. 5,364,399 discloses an anterior cervical plate system in which the openings through the plate guide the screws in a non-perpendicular orientation that causes the screws to diverge, rather than converge, as they proceed into the particular cervical vertebra. The plate has a recess for limiting the degree of outward protrusion of the screw heads. After each pair of screws is fully inserted, a locking screw is threaded into the plate until its head encounters the heads of the bone screws.

U.S. Patent Publication No. 2005/0021032 discloses a cervical spine fixator including screw head fixture members having a protruder, which is deformed under the effect of pressure by a screw head when the screws are inserted and returns to their position of origin when the screw head is completely accommodated into the plates. The plates include receiving grooves communicating with the respective apertures, where the grooves are for accommodating the screw head and the screw head fixture member. Among the disadvantages of this design is the weakening of the plate in the area of the apertures due to the receiving grooves. This weakening may cause failure of the device under loading conditions.

U.S. Pat. No. 6,626,907 discloses an anterior cervical plate that uses threaded fasteners through respective apertures for securing the plate to vertebrae. The cervical plate incorporates a fastener retaining feature in the form of a cantilevered tab or a beam supported at its opposite ends, and plastically deformable between an open position for admitting the fastener and a closed position for preventing retraction. A disadvantage of this approach to securing the screws is again the requirement for a recess or groove in the area of the aperture to accommodate the deformable retaining feature. Further, as the retaining feature must be bent (past its point of elasticity) there is the possibility of breaking the retaining feature during the surgery. Depending on when the breakage occurs, this might require the removal of a number of screws that have already been tightened down, a very undesirable necessity. The screw removal problem is exacerbated by the retainer feature itself, as it cannot be easily reversed. Indeed, once deformed, the cold work of the material makes it more difficult to reverse the deformation process to remove the screws.

Therefore, conventional devices for screw retention have not provided a comprehensive, simple, and reliable means of counteracting the tendency of the bone screws to work loose after cervical plate fixation.

SUMMARY OF THE INVENTION

In accordance with one or more embodiments of the present invention, a skeletal fixation apparatus includes: a plate having first and second spaced apart surfaces and a plurality of apertures extending through the surfaces of the plate, each aperture for receiving a respective fixation element for coupling the plate to one or more bones of a patient; and at least one retention element having an elongate member coupled to the plate at first and second ends thereof, wherein the first end of the elongate member is fixed in position and the second end of the elongate member is operable to rotate about the first end such that: (i) at least a portion of the elongate member overlies at least a portion of a first of the apertures when the second end is in at least one first rotational position to retain a first fixation element in the first aperture, and (ii) the elongate member does not substantially overlie the first aperture when the second end is in at least one second rotational position to permit the first fixation element to enter or exit the first aperture.

The plate may be of a length sufficient to extend over an intervertebral space of the patient's spine and include at least one aperture, and associated retention element, at respective longitudinal ends thereof for coupling the plate to respective vertebral bones. Alternatively, the plate may be of a length sufficient to extend over a plurality of intervertebral spaces of the patient's spine and include at least one aperture, and associated retention element, at respective longitudinal positions thereof for coupling the plate to respective vertebral bones.

In accordance with one or more further embodiments of the present invention, a skeletal fixation apparatus includes: a plate having first and second spaced apart surfaces and at least first and second apertures extending through the surfaces of the plate, each aperture for receiving a respective fixation element for coupling the plate to one or more bones of a patient; and at least one retention element having an elongate member coupled to the plate at a first end, a first intermediate position, second intermediate position, and a second end thereof, wherein the first and second intermediate positions of the elongate member are fixed in position, and the first and second ends of the elongate member are operable to rotate about the respective first and second intermediate positions such that: (i) at least first and second portions of the elongate member overlie portions of the first and second apertures, respectively, when the respective first and second ends are one or more first rotational positions, respectively, to retain respective fixation elements in the first and second apertures, and (ii) the first and second portions of the elongate member do not substantially overlie the first and second apertures, respectively, when the first and second ends are in one or more second rotational positions, respectively, to permit the fixation elements to enter or exit the first and second apertures.

In accordance with one or more further embodiments of the present invention, a tool for turning a bone screw includes: a shaft having a first end and a second end, the second end operable to engage a head of the bone screw; a sleeve having a first end and a second end and including a longitudinal bore sized and shaped to receive the shaft such that the shaft may rotate within and slide therethrough, wherein the second end of the sleeve includes an engagement element operable to manipulate a bone screw retention element of a skeletal fixation apparatus while the second end of the shaft engages the head of the bone screw.

Other aspects, features, advantages, etc. will become apparent to one skilled in the art when the description of the preferred embodiments of the invention herein is taken in conjunction with the accompanying drawings.

BRIEF DESCRIPTION OF THE DRAWINGS

For the purposes of illustrating the various aspects of the invention, there are shown in the drawings forms that are presently preferred, it being understood, however, that the invention is not limited to the precise arrangements and instrumentalities shown.

DETAILED DESCRIPTION

It is noted that various aspects of the present invention may be employed in any application in which a screw (or other attachment device) is used to fasten a structure to an anatomical body. For the purposes of discussion, and not by way of limitation, various aspects of the present invention will be presented in connection with a number of embodiments directed to a specific application in which spinal stabilization (e.g., fusion) is desired.

In this regard, reference is now made to the drawings, wherein like numerals indicate like elements. There is shown in FIGS. 1-6 a skeletal fixation apparatus in accordance with one or more embodiments of the present invention. The skeletal fixation apparatus in this embodiment is implemented as a bone plate 100 that is suitable for use in fusing adjacent vertebrae in a spine. It is understood that the bone plate 100 may be employed at any level of the spine (cervical, thoracic, lumbar) by suitable adjustment in the various dimensions thereof. The bone plate 100 is preferably sized and shaped for use on an anterior aspect of the spine.

In this embodiment, the bone plate 100 is specifically designed for single-level spinal fixation (although multi-level applications are also contemplated as will be discussed later herein). The bone plate 100 may be used at various stages of spinal disc degeneration disease in order to fuse the vertebral bones of adjacent vertebrae to eliminate most ranges of motion. It is understood that the use of the various embodiments of the bone plate 100 includes a plate 102 formed from a suitable biologically acceptable material, such as stainless steel, titanium, and/or any other metal or metal alloy. The plate 102 includes first and second spaced apart surfaces 104, 106 that are preferably in a parallel orientation.

Figure 1:
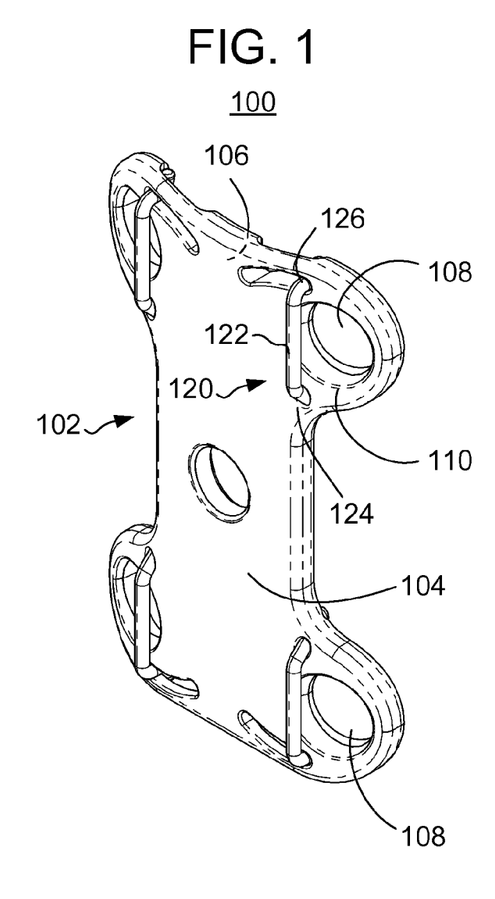
FIG. 1 is a perspective view of a stabilizer system in accordance with one or more embodiments of the present invention.
Figure 2:
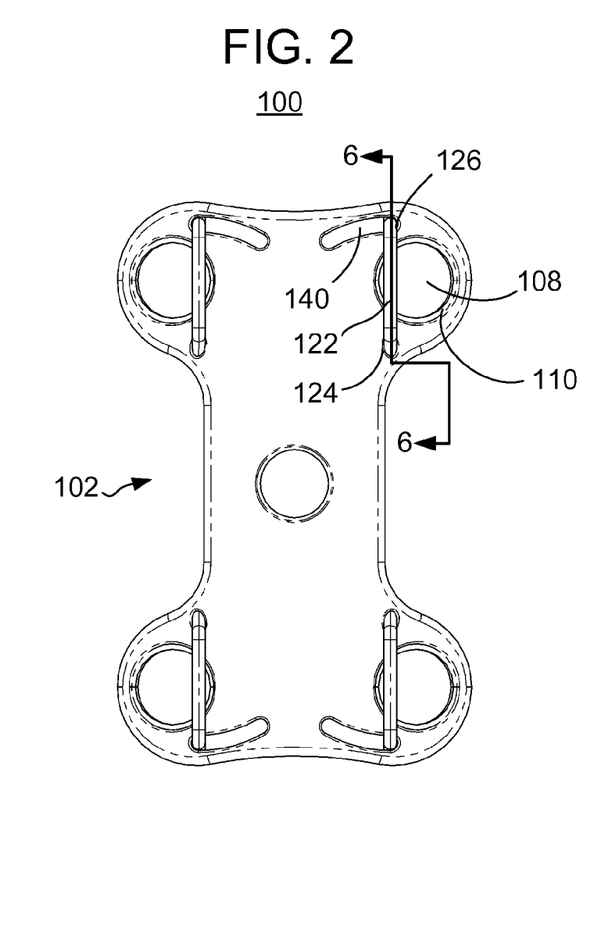
FIG. 2 is a front elevational view of the stabilizer of FIG. 1.
Figure 5:
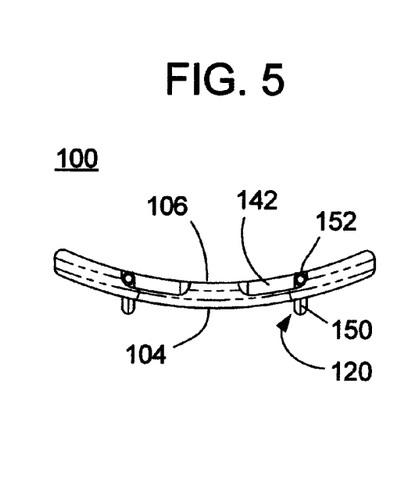
FIG. 5 is top view of the stabilizer of FIG. 1.

As best seen in FIGS. 1 and 5, the plate 102 is bowed (or curved) in a lateral aspect in order to complement the natural curvature of vertebral bones of the spine. In addition, the plate 102 is T-bone shaped to accommodate other natural aspects of the spinal anatomy.

The plate 102 includes a plurality of apertures 108 extending through the first and second surfaces 104, 106. The apertures 108 are sized and shaped to receive respective anchoring screws 10 (best seen in FIGS. 3 and 11), such as commonly available bone screws known to those skilled in the art. Each bone screw 10 engages a respective periphery 110 of an associated aperture 108 in order to fix the bone plate 100 to respective vertebral bones of the spine. The bone plate 100 preferably includes at least one aperture 108 disposed at respective longitudinal ends thereof for fastening the bone plate 100 to the respective vertebral bones. Two apertures 108 are preferably disposed at the respective longitudinal ends of the bone plate 100 to insure satisfactory connection of the bone plate 100 to the respective intervertebral bones.

The bone plate 100 preferably includes one or more retention elements 120 that operate to prevent the bone screws 10 from backing out of the apertures 108 after the bone plate 100 has been secured to the vertebral bones of the spine. In a preferred embodiment, a respective retention element 120 is disposed at each of the plurality of apertures 108. The retention element 120 includes an elongate member 122 having a first end 124 that is coupled to the bone plate 100 adjacent to the associated aperture 108, and a second end 126 that is also coupled to the bone plate 100 adjacent to the aperture 108. The first end 124 of the elongate member 122 may be fixed in position, while the second end 126 thereof may be operable to rotate about the first end 124.

In its resting position, at least a portion of the elongate member 122 of the retention element 120 overlies at least a portion of the aperture 108. In this resting position, the second end 124 of the elongate member 122 is in at least one first rotational position 130 (see FIG. 3) such that the elongate member 122 may retain the bone screw 10 within the aperture 108 and prevent same from backing out of the aperture 108 and/or loosening the connection of the bone plate 100 to the vertebral bone. As the second end 126 of the elongate member 122 may rotate, there is at least one second rotational position 132 (see FIG. 3) in which the elongate member 122 does not substantially overlie the aperture 108 and permits the bone screw 10 to enter and/or exit the aperture 108.

Figure 3:
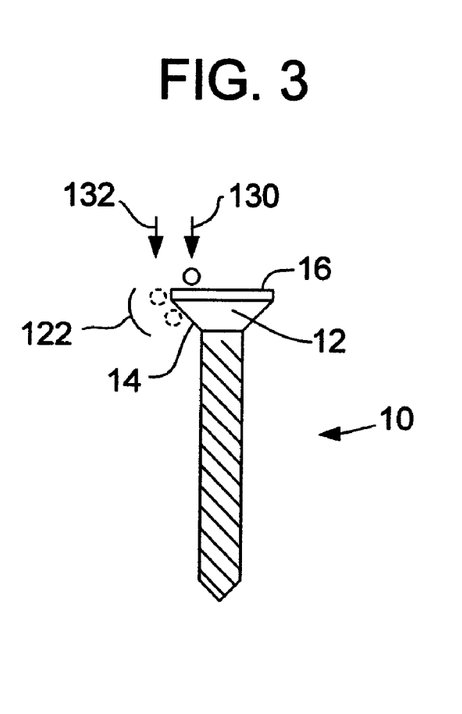
FIG. 3 is a side view of a retaining feature of the stabilizer of FIG. 1.

As shown in FIG. 3, the elongate member 122 is operable to engage the head 12 of the bone screw 10 (particularly the upper surface 16 thereof) to retain same within the aperture 108. The elongate member 122 may be positioned off-center relative to the aperture 108 such that the head 12 of the bone screw 10 urges the elongate member 122 aside, thereby rotating the second end 126 thereof to or toward the second rotational position 132 as the bone screw 10 is driven into the bone. A chamfered surface 14 of the head 12 may assist in urging the elongate member 122 aside. When the head 12 substantially engages the periphery 110 of the aperture 108, the elongate member 122 may clear the upper surface 16 of the bone screw 10 such that the elongate member 122 rotates back and the second end 126 thereof moves back to or toward the first rotational position 130.

Preferably, the rotation of the second end 126 of the elongate member 122 away from the resting position results in a bias force back towards the first rotational position 130. For example, the first end 124 of the elongate member 122 may be coupled to the bone plate 100 such that rotation of the second end 126 of the elongate member 122 towards the second rotational position 132 causes a counter torsional force urging the second end 126 of the elongate member 122 toward the first rotational position 130. The first end 124 of the elongate member 122 may be rigidly fixed to the bone plate 100 by way of a suitable engagement into an aperture thereof. The counter torsional force may be developed as a result of the elastic material properties of the elongate member 122 as the first end 124 of the elongate member 122 is prevented from swiveling relative to the bone plate 100. These elastic material properties may manifest in a spring bias of the second end 126 of the elongate member 122 toward the first rotational position 130.

The second end 126 of the retention element 120 is preferably slidingly coupled to the bone plate 100. In one or more embodiments, the retention element 120 may include a slot 140 extending from the first surface 104 of the bone plate 100 and at least partially through the plate 100. In one or more preferred embodiments, the slot 140 extends completely through the bone plate 100 from the first surface 104 to the second surface 106. The second end 126 of the elongate member 122 is preferably slidingly engaged in the slot 140. In one or more embodiments, the slot 140 may extend longitudinally along an arc, which is sized and shaped to complement the natural arc through which the second end 126 sweeps as it rotates from the first rotational position 130 to the second rotational position 132. Thus, the arc may have a fulcrum substantially where the first end 124 of the elongate member 122 connects to the plate 100. The second end 126 of the elongate member 122 may, therefore, slide along the arc of the slot 140 as it rotates.

Figure 4:
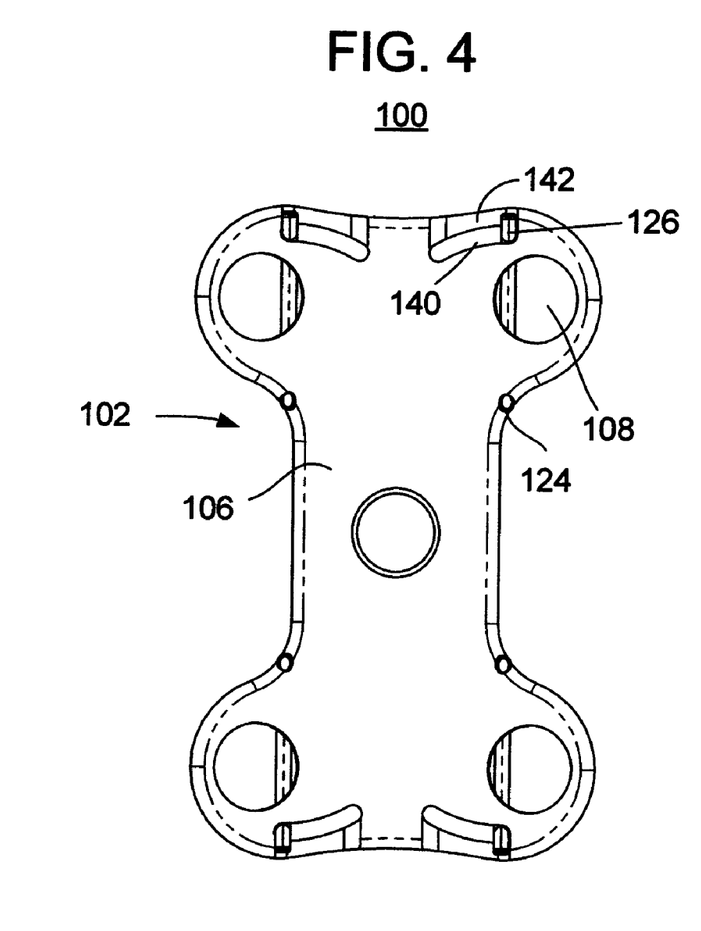
FIG. 4 is a rear elevational view of the stabilizer of FIG. 1.

As best seen in FIGS. 4 and 5, the second end 126 of the elongate member 122 may extend through the slot 140 at least toward the second surface 106 of the plate 100. The retention element 120 may further include a recess 142 extending from the second surface 106 of the plate 100 toward the first surface 104 thereof. The recess 142 preferably communicates with the slot 140 such that the second end 126 of the elongate member 122 slidingly engages the recess 142 as it rotates. The recess 142 as well as the orientation and design aspects of the second end 126 of the elongate member 122 are preferably sized and shaped such that the second end 126 does not extend beyond a plane of the second surface 106 of the bone plate 100. Thus, when the bone plate 100 is pressed against the vertebral bone of the spine, the elongate member 122 of the retention element 120 is permitted to rotate without the second end 126 thereof interfering with the vertebral bone.

Figure 6:
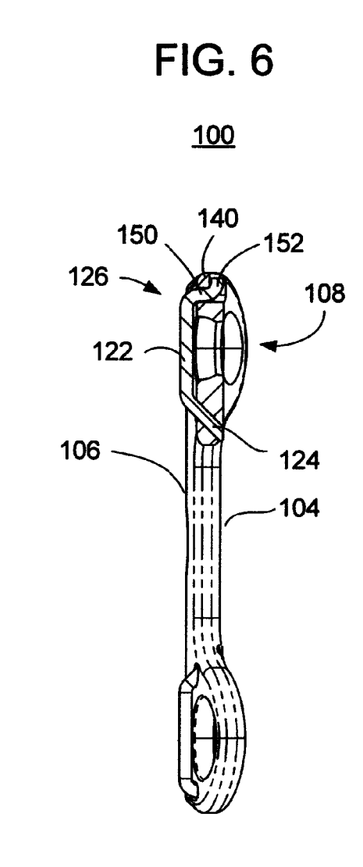
FIG. 6 is a partial cross-sectional view of the stabilizer of FIG. 2 taken through line 6-6.

As best seen in the partial cross-sectional view of the bone plate 100 as illustrated in FIG. 6, a first length 150 of the second end 126 of the elongate member 122 extends transversely from the portion thereof overlying the aperture 108. The first length 150 is the portion of the second end 126 that passes through the slot 140. A second length 152 of the second end 126 of the elongate member 122 may extend transversely from the first length 150 to engage the recess 142 (and/or the slot 140) such that the second end 126 cannot disengage from the slot 140.

As best seen in FIG. 6, the first end 124 of the elongate member 122 preferably extends transversely with respect to the portion thereof overlying the aperture 108 as it enters the bone plate 100. It is preferred that the first end 124 extends obliquely into the bone plate 100 with respect to the portion thereof overlying the aperture 108. By extending the first end 124 obliquely with respect to the elongate member 122, the tendency for the first end 124 to slip within the aperture into which it is inserted may be mitigated. The first end 124 of the elongate member 122 is preferably fixed to the bone plate 100 by way of a stiff press fit into the aperture of the bone plate 100, which prevents rotational slippage and extraction thereof. It is noted, however, that the oblique extension of the first end 124 into the bone plate 100 permits a loose (or absent) press fit because a pivot force at the point of inflection on the first end 124 is countered by a moment arm formed by the length of the first end 124 within the bone plate 100. In an alternative embodiment, the first end 124 of the elongate member 122 may extend perpendicularly into the bone plate 100. The torsional forces applied to the first end 124, therefore may tend to cause rotational slippage and/or disengagement of the first end 124 from the bone plate 100. Accordingly, when a perpendicular entry is contemplated, a tight press fit should be employed.

Figure 7:
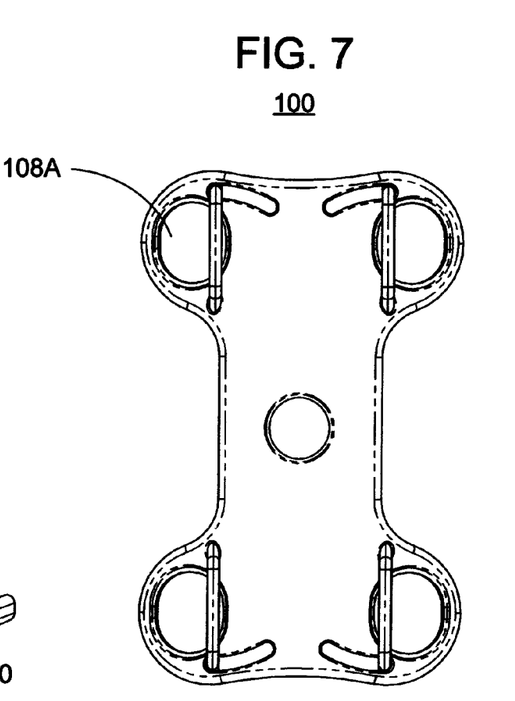
FIG. 7 is a front elevational view of an alternative embodiment of a stabilizer system in accordance with one or more further aspects of the present invention.

While all of the apertures 108 illustrated in FIGS. 1-6 are substantially round, one or more of the apertures 108A may be elongate as illustrated in FIG. 7.

Figure 8:
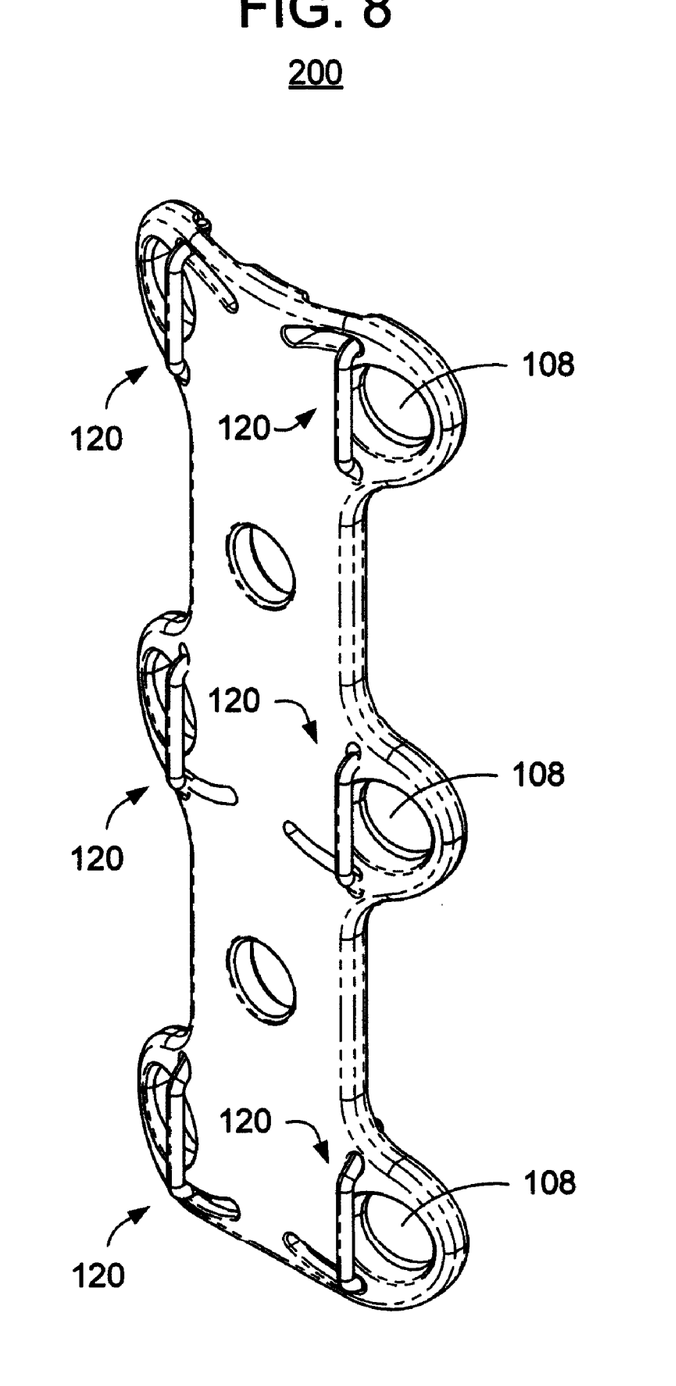
FIG. 8 is a perspective view of a further alternative embodiment of a stabilizer system in accordance with one or more further aspects of the present invention.

As best seen in FIG. 8, alternative embodiments suitable for multi-level spinal fixation are also contemplated. The bone plate 200 includes a length sufficient to extend over a plurality of intervertebral spaces (in this example, two such spaces) of the patient's spine. The bone plate 200 includes one or more apertures 108, one or more of which (and preferably all of which) include an associated retention element 120 at respective longitudinal positions of the plate 200 for coupling the plate to the respective vertebral bones. Those skilled in the art will appreciate that the number and extent of multi-level spinal fixation is not limited to two; indeed, any practical number of intervertebral spaces may be treated by implementing the bone plate with an appropriate length and number of apertures 108.

Figure 9:
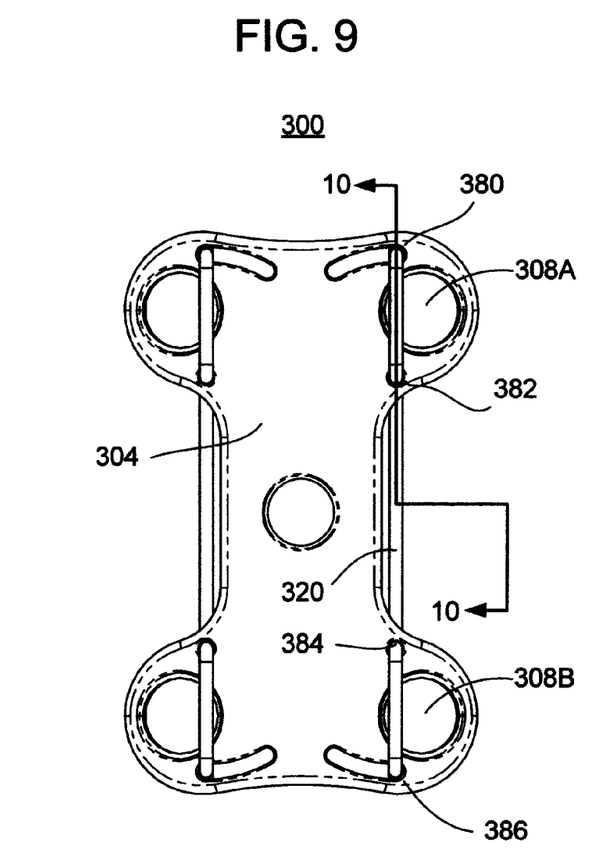
FIG. 9 is a front elevational view of a further alternative embodiment of a stabilizer system in accordance with one or more further aspects of the present invention.
Figure 10:
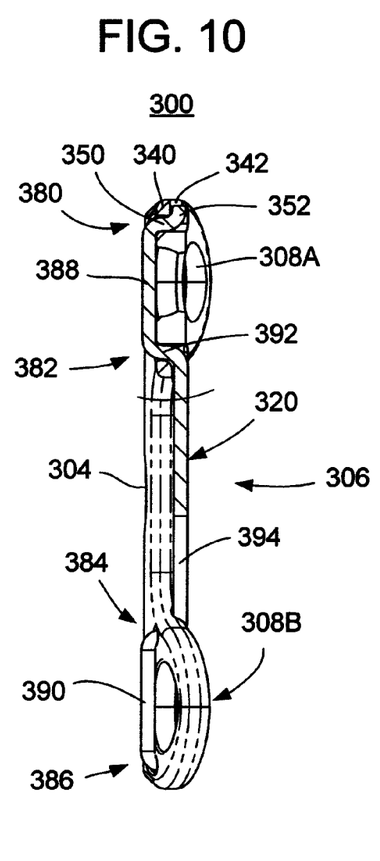
FIG. 10 is a partial cross-sectional view of the stabilizer of FIG. 9 taken through line 10-10.

Reference is now made to FIGS. 9 and 10, which illustrate an alternative embodiment of a bone plate 300 in accordance with one or more further aspects of the present invention. FIG. 9 is a front view of the bone plate 300, while FIG. 10 is a partial cross-sectional view of the bone plate 300 of FIG. 9 taken through line 10-10. The plate 300 includes first and second apertures 308A, 308B extending through the surfaces 304, 306 of the plate 300. A retention element 320 is coupled to the plate 300 at the following points: a first end 380, a first intermediate position 382, a second intermediate position 384, and a second end 386. The first and second intermediate positions 382, 384 of the retention element 320 may be fixed in position (similar to the restraint on movement of the first end 124 of the elongate member 122 discussed hereinabove).

The first and second ends 380, 386 of the retention element 320 are operable to rotate about the first and second intermediate positions 382, 384, respectively, in substantially the same way as the second end 126 of the retention element 120 discussed above. Thus, first and second portions 388, 390 of the retention element 320 overlie portions of the first and second apertures 308A, 308B, respectively, when the first and second ends 380, 386 are in one or more first rotational positions, respectively. Thus, the portions 388, 390 of the retention element 320 may retain respective bone screws in the first and second aperture 308A, 308B as discussed above with respect to prior embodiments of the invention. Similarly, the first and second portions 388, 390 may be moved or rotated such that they do not substantially overlie the first and second apertures 308A, 308B, respectively, when the first and second ends 380, 386 are in one or more second rotational positions, respectively. Thus, the bone screws 10 may be permitted to enter or exit the apertures 308A, 108B as discussed hereinabove with respect to prior embodiments of the invention.

As best seen in FIG. 10, the retention element 320 may be formed from a contiguous piece of wire that has been appropriately bent to achieve the aforementioned functionality. A first length 350 of the first end 380 of the retention element 320 may extend transversely with respect to the first portion 388 as it passes through a first slot 340. A second length 352 of the first end 380 may extend transversely from the first length 350 to engage a recess 342 (and/or the slot 340) such that the first end 380 of the retention element 320 does not disengage from the slot 340. A portion 392 of the first intermediate position 382 may extend transversely with respect to the first portion 388 as it passes through the bone plate 300 from the first surface 304 to the second surface 306. The retention element 320 extends along the second surface 304 between the first and second intermediate portions 382, 384. A length (not visible) of the second intermediate position 384 may extend transversely from the length 394 as it passes through the bone plate 300 from the second surface 306 to the first surface 304. Further details regarding the second portion 390 and the second end 386 of the retention element 320 are substantially similar to those discussed above with respect to the first end 380.

As the retention element 320 passes through the bone plate 300 at the first and second intermediate positions 382, 384, respective apertures for committing the wire to pass through the bone plate 300 need not tightly grip the wire. Indeed, the apertures may be oversized to permit the wire to easily slide through the bone plate 300. Further, the transverse orientation of the wire as it passes through the bone plate need not be oblique (although it may be) because the first and second intermediate positions 382, 284 effectively anchor those positions and permit the aforementioned rotation and biasing forces with respect to the first and second ends 380, 386 of the retention element 320.

Figure 11:
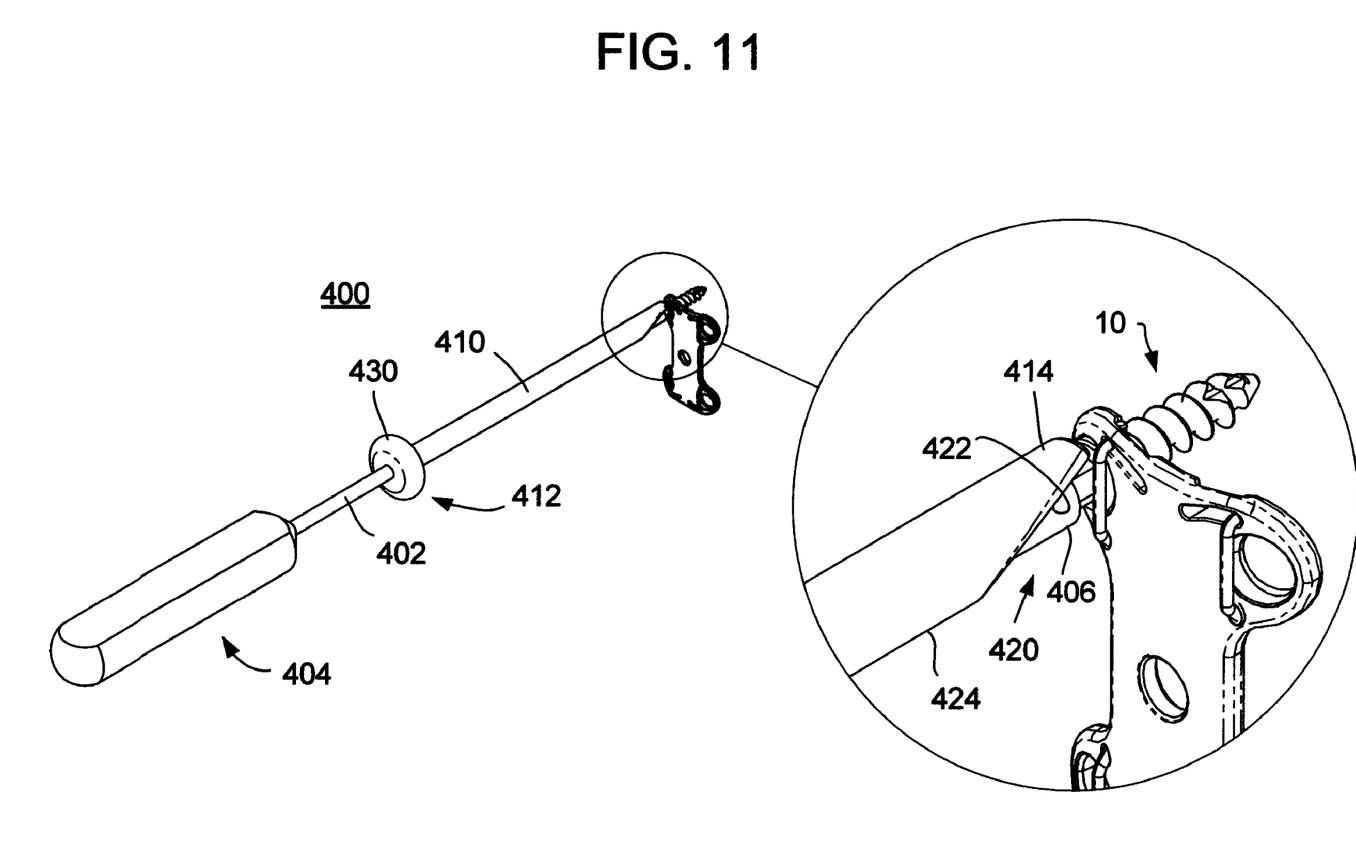
FIG. 11 is a perspective view of an instrument for attaching the stabilizer of FIG. 1 (or any other embodiments) to bones of a patient.

Reference is now made to FIG. 11, which illustrates a tool 400 for inserting or removing the bone screw 10. The tool 400 includes a shaft 402 having a first end 404 and a second end 406. The second end 406 is operable to engage the head 12 of the bone screw 10. By way of example, the second end 406 of the shaft 402 may include an appropriate polygonal profile, such as a hex-head shape. The first end 404 of the shaft 402 is operable to permit a user to turn the shaft 402, such as by way of a handle. Thus, turning the first end 404 of the tool 400 in one direction or the other facilitates driving the screw 10 into the bone or removing the screw 10 from the bone. The tool 400 also includes a sleeve 410 having a first end 412 and a second end 414. The sleeve 410 includes a longitudinal bore extending from the first end 412 to the second end 414, where the bore is sized and shaped to receive the shaft 402 and permit the shaft 402 to rotate within and slide through the sleeve 410.

The second end 414 of the sleeve 410 includes an engagement element 420 operable to manipulate the retention element 120 (or 320) discussed hereinabove. Notably, the engagement element 420 may manipulate the retention element 120 while the second end 406 of the shaft 402 engages the head 12 of the bone screw 10, even as the shaft 402 is driving or removing the screw 10. In a preferred embodiment, the engagement element 420 includes a tapered surface 422 extending from an outer surface 424 of the sleeve 410 toward the second end 414 thereof. The tapered surface 422 of the engagement element 420 may urge the retention element 120 into the second rotational position 132 by rotating the sleeve 410 about the shaft 402. The sleeve 410 may include a rotation assistance device 430 at the first end thereof, such as a thumb wheel.

Some notable features of the aforementioned retaining element are listed below, it being understood that various features alone or in combination may be employed: a screw back-out prevention element is provided; a low-profile mechanism secured to plate exterior or interior is provided; a low plate thickness is achieved; provide retention with various any screw angulations; a self-locking screw insertion feature is provided; may accommodate uniform or variable plate thicknesses; both methods and instrumentation for screw removal and retention are provided; and the apparatus is soft-tissue friendly.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An apparatus, comprising:
a plate having first and second spaced apart surfaces and at least first and second apertures extending through the surfaces of the plate, each aperture for receiving a respective fixation element for coupling the plate to one or more bones of a patient; and
at least one retention element having an elongate member coupled to the plate at least at a first end, a plurality of intermediate positions, and a second end thereof, wherein:
the plurality of intermediate positions of the elongate member include at least a first intermediate position and a second intermediate position that are fixed in position,
the elongate member, between the first end and the first intermediate position, extends along the first surface of the plate,
the elongate member, between the first and second intermediate positions, extends along the second surface of the plate,
the elongate member, between the second intermediate position and the second end, extends along the second surface of the plate, and
the first and second ends of the elongate member are operable to rotate about the respective first and second intermediate positions such that:
(i) at least first and second portions of the elongate member overlie portions of the first and second apertures, respectively, when the respective first and second ends are in one or more first rotational positions, respectively, to retain respective fixation elements in the first and second apertures, and
(ii) the first and second portions of the elongate member do not substantially overlie the first and second apertures, respectively, when the first and second ends are in one or more second rotational positions, respectively, to permit the fixation elements to enter or exit the first and second apertures.

2. The apparatus of claim 1, wherein the elongate member is formed from a contiguous piece of wire.

3. The apparatus of claim 1, further comprising at least first and second slots disposed at the first and second ends of the elongate member, respectively, each slot extending from the first surface and at least partially through the plate, wherein the first and second ends of the elongate member are slidingly engaged in the first and second slots, respectively.

4. The apparatus of claim 3, wherein:
the first and second slots extend longitudinally along respective arcs, the arcs having fulcrums substantially where the first and second intermediate positions, respectively, connect to the plate; and
the first and second ends of the elongate member slide along the arcs, respectively, as they rotate between the first and second rotational positions.

5. The apparatus of claim 4, wherein:
the first and second slots extend through the plate from the first surface to the second surface; and
the apparatus further comprises first and second recesses extending from the second surface of the plate toward the first surface thereof, and each communicating with one of the first and second slots, such that the first and second ends of the elongate member slidingly engage the first and second recesses, respectively, as they rotate.

6. The apparatus of claim 5, wherein:
a first length of each of the first and second ends of the elongate member extends transversely from the portion thereof overlying the respective first and second apertures as it passes through the respective first and second slot; and
a second length of each of the first and second ends of the elongate member extend transversely from the first length to engage the respective first and second recesses such that the first and second ends of the elongate member cannot disengage from the first and second slots.

7. The apparatus of claim 6, wherein:
the elongate member, between the first end and the first intermediate position, extends along the first surface of the plate;
the elongate member, between the first and second intermediate positions, extends along the second surface of the plate; and
the elongate member, between the second intermediate position and the second end, extends along the second surface of the plate.

8. The apparatus of claim 7, wherein the elongate member is formed from a contiguous piece of wire.

9. The apparatus of claim 1, wherein the plate is of a length sufficient to extend over a plurality of intervertebral spaces of a spine of the patient and includes at least one further aperture, and associated retention element, at respective longitudinal positions thereof for coupling the plate to respective vertebral bones of the patient.

10. An apparatus, comprising:
a plate having first and second spaced apart surfaces and at least first and second apertures extending through the surfaces of the plate, each aperture for receiving a respective fixation element for coupling the plate to one or more bones of a patient;
at least one retention element having an elongate member coupled to the plate at least at a first end, a plurality of intermediate positions, and a second end thereof, wherein the plurality of intermediate positions of the elongate member include at least a first intermediate position and a second intermediate position that are fixed in position; and at least first and second slots disposed at the first and second ends of the elongate member, respectively, each slot extending from the first surface and at least partially through the plate, and each slot extending longitudinally along respective arcs, the arcs having fulcrums substantially where the first and second intermediate positions, respectively, connect to the plate, wherein:

the first and second ends of the elongate member are operable to rotate about the respective first and second intermediate positions such that:

(i) at least first and second portions of the elongate member overlie portions of the first and second apertures, respectively, when the respective first and second ends are in one or more first rotational positions, respectively, to retain respective fixation elements in the first and second apertures, (ii) the first and second portions of the elongate member do not substantially overlie the first and second apertures, respectively, when the first and second ends are in one or more second rotational positions, respectively, to permit the fixation elements to enter or exit the first and second apertures, and (iii) the first and second ends of the elongate member are slidingly engaged in the first and second slots, respectively, such that the first and second ends of the elongate member slide along the arcs, respectively, as they rotate between the first and second rotational positions.

11. The apparatus of claim 10, wherein:

the first and second slots extend through the plate from the first surface to the second surface; and the apparatus further comprises first and second recesses extending from the second surface of the plate toward the first surface thereof, and each communicating with one of the first and second slots, such that the first and second ends of the elongate member slidingly engage the first and second recesses, respectively, as they rotate.

12. The apparatus of claim 11, wherein:

a first length of each of the first and second ends of the elongate member extends transversely from the portion thereof overlying the respective first and second apertures as it passes through the respective first and second slot; and a second length of each of the first and second ends of the elongate member extend transversely from the first length to engage the respective first and second recesses such that the first and second ends of the elongate member cannot disengage from the first and second slots.

13. The apparatus of claim 12, wherein:

the elongate member, between the first end and the first intermediate position, extends along the first surface of the plate;

the elongate member, between the first and second intermediate positions, extends along the second surface of the plate; and the elongate member, between the second intermediate position and the second end, extends along the second surface of the plate.

14. The apparatus of claim 13, wherein the elongate member is formed from a contiguous piece of wire.

* * * * *